United States Patent [19]

Hardy

[11] 4,407,765

[45] Oct. 4, 1983

[54] SYNTHESIS OF ORGANIC PHOSPHATE-PHOSPHONATES

[75] Inventor: Thomas A. Hardy, Fairfield, Conn.

[73] Assignee: Stauffer Chemical Company, Westport, Conn.

[21] Appl. No.: 332,394

[22] Filed: Dec. 21, 1981

Related U.S. Application Data

[63] Continuation of Ser. No. 165,428, Jul. 2, 1980, abandoned.

[51] Int. Cl.$^3$ ................................................ C07F 9/09
[52] U.S. Cl. .................................... 260/970; 260/931; 260/935; 260/969
[58] Field of Search ......................................... 260/970

[56] References Cited

U.S. PATENT DOCUMENTS 3,042,702  7/1962  Birum ................................... 260/931
3,676,532  7/1972  Turley ................................... 260/931

OTHER PUBLICATIONS

Crammer, "Angew. Chem." 72, (1960), pp. 236 and 239.
Pudovik et al., "Zhurnal Obshchei Khimii, English Translation of vol. 48, #6, (1978) pp. 1420–1421.

Primary Examiner—Anton H. Sutto
Attorney, Agent, or Firm—Roger S. Benjamin

[57] ABSTRACT

A process for the preparation of organic phosphate-phosphonates comprises the steps of reacting an organic acylating agent with an organophosphite triester to form an intermediate followed by reacting the intermediate with an organophosphite diester.

Typically benzoyl chloride is the acylating agent, triethyl phosphite and bis ($\beta$-chloroethyl) phosphite the sequential reactants, and the second step is carried out in the presence of a catalytic amount of a tertiary amine. A solvent such as methylene dichloride may be employed.

Organic phosphate-phosphonates are useful as flame retardants, especially in urethane foams.

13 Claims, No Drawings

SYNTHESIS OF ORGANIC PHOSPHATE-PHOSPHONATES

This is a continuation of application Ser. No. 165,428, filed July 2, 1980, now abandoned.

BACKGROUND OF THE INVENTION

1. Field of the Invention

This invention relates to the synthesis of organic phosphate-phosphonates.

Phosphite-phosphonates can be made by the reaction of phosphorus trichloride with symmetrically disubstituted ethylene oxide followed by reaction with an acylating agent, especially an aldehyde, phosphite-phosphonates can be oxidized to phosphate-phosphonates.

Another route to phosphate-phosphonates involves the condensation of two moles of a dialkyl phosphite with an acid chloride in the presence of a molar amount of an acid acceptor such as triethylamine.

Reaction of a phosphorohalidite with an aldehyde and a trivalent phosphorus ester also produces organic phosphate-phosphonates.

Rearrangement of 1-hydroxyalkylidenediphosphonate esters yields the related phosphate-phosphonate.

When vinyl acetate is caused to react with a dialkyl hydrogen phosphite, the appropriate phosphate-phosphonate can be produced.

2. Description of the Prior Art

In U.S. Pat. No. 3,676,532 granted July 11, 1972 Turley discloses a method for preparing alkyl phosphate-phosphonates by condensing dialkyl phosphites with aroyl halides using tertiary alkylamines as hydrohalogen acid acceptors.

In U.S. Pat. Nos. 3,042,701 granted July 3, 1962 and 3,014,956 granted Dec. 26, 1961 Birum discloses haloalkyl phosphate-phosphonates prepared by reacting a phosphorohalidite with an aldehyde and a phosphorus triester.

In U.S. Pat. Nos. 3,014,951 and 3,014,944 Birum discloses a large number of phosphite-phosphonates made by condensing substituted oxiranes with phosphorus trihalide and aldehydes or ketones. Phosphite-phosphonates can be converted to phosphate-phosphonates by the methods disclosed in Birum patents U.S. Pat. Nos. 3,042,701 and 3,014,956.

In U.S. Pat. Nos. 2,924,553 granted Feb. 9, 1960 and 2,900,296 granted Aug. 18, 1959 Baker and Saul disclose preparation of a dialkyl benzoylphosphonate from reaction of a substituted benzoyl with a trialkyl phosphite. A similar reaction is disclosed by Ernsberger in U.S. Pat. No. 2,491,920 granted Dec. 20, 1949.

The rearrangement of a tetraalkyl 1-hydroxyalkylidenediphosphonate to the related phosphate-phosphonate ester has been published by Fitch and Moedritzer, Abstr. 140th ACS Mtg, Chicago, 41Q, Sept. 3, 1961; J. Am. Chem. Soc. 84, 1876 (1962); by Pudovik et al., Dokl. Akad. Nauk SSSR 143, 875 (1962); ibid 153, 616 (1963); and by Nicholson and Vaughn, J. Org. Chem. 36, 3843 (1971).

OBJECTS OF THE INVENTION

The principal object of the invention is to prepare organic phosphate-phosphonates in a single reactor from readily available raw materials without generating corrosive byproducts such as hydrogen chloride.

An additional object of the invention is to prepare phosphate-phosphonates employing only catalytic amounts of a Lewis base such as triethylamine.

A further object of the invention is to prepare purified phosphate-phosphonates without having to subject the product to the degradative effects of distillation.

Still a further object of the invention is to save energy in the preparation of phosphate-phosphonates by distilling only low boiling solvents.

Still another object of the invention is to prepare phosphate-phosphonates without the necessity of handling hazardous and corrosive phosphorus halides.

Other objects of the invention will be apparent to those skilled in the art by inspection of the following description and Examples.

SUMMARY OF THE INVENTION

The present invention is a process for the preparation of organic phosphate-phosphonates comprising the steps of reacting an organic acylating agent with an organophosphite triester to form an intermediate followed by reacting the intermediate with an organophosphite diester.

Either or both steps may be carried out in a solvent, preferably a low-boiling halocarbon. The second step is facilitated by the presence of a Lewis base such as triethylamine in catalytic amounts.

The preferred acylating agents are acid chlorides such as acetyl chloride or benzoyl chloride. The preferred phosphite triesters and phosphite diesters are alkyl or haloalkyl derivatives such as ethyl or β-chloroethyl phosphites.

Organic phosphate-phosphonates are useful as flame retardants, especially for polyurethane foams.

DESCRIPTION OF THE INVENTION

Tetraalkyl phosphate-phosphonates, also called phosphorus diesters or (α-dialkoxyphosphinyl)alkylidene phosphates have previously been prepared by processes which involve phosphorus trihalides directly or indirectly. Consequently molar amounts of hydrogen chloride are generated and thus molar amounts of a base must be present to facilitate replacement on the phosphorus atom. The present invention employs alkyl phosphites, that is oxygenated phosphorus throughout and eschews formation of hydrogen chloride. Only catalytic amounts of organic base are thus required.

The instant invention is carried out in two steps. In the first step an acylating agent reacts with a triphosphite to form an intermediate. In the second step the intermediate reacts with a diphosphite to form the phosphate-phosphonate:

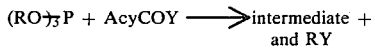

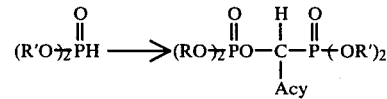

The following equations illustrate the process of the present invention for the case when R=R'=ethyl and acetyl chloride is the acylating agent. These equations are intended solely as an aid to understanding the instant invention and may not in fact depict the chemistry of the invention, which is easily practiced without detailed knowledge of its actual chemistry:

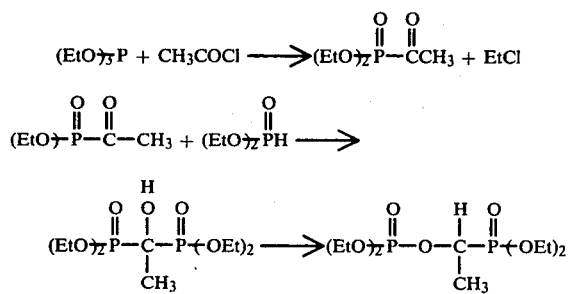

The equations above represent the case of a symmetrical hydroxy-biphosphonate rearranging to give a single phosphate-phosphonate, namely the tetraethyl derivative. If the alkyl phosphite triester and the alkyl phosphite diester of the starting materials bear different alkyl, or haloalkyl groups, then an unsymmetrical hydroxy-biphosphonate is believed to form. Upon rearrangement both possible phosphate-phosphonates would be formed in approximately equal amounts. This is, for the case of acetylchloride, triethyl phosphite, and dimethyl phosphite as starting materials both isomeric phosphate-phosphonates are formed by the process of the present invention in about equal amounts:

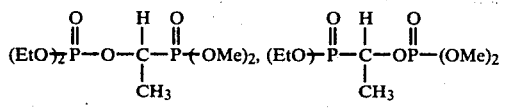

The acylating agent which is the source of the alkylidene moiety linking the phosphate and phosphonate groups in the product of the process of the present invention normally has a carbonyl group. The acylating agent may be an acid chloride, an acid bromide, an acid anhydride, an acid, an amide, a N-substituted amide, or an ester. The preferred acylating agents are benzoyl and substituted benzoyl chlorides and acyl chlorides having two to nine carbon atoms. Thioacylating agents may also be used in which case thiophosphate-phosphonates would be produced, as disclosed in U.S. Pat. No. 3,042,701. The acylating agent may have halogen atoms, nitro, cyano groups, carboalkoxy, alkoxy, alkylthio groups, thienyl, furyl radicals or any mixture of these moieties substituted thereon.

The organic phosphite triester of the first step, which reacts with the acylating agent, normally is a simple or mixed alkyl or haloalkyl triphosphite wherein each alkyl group has one to eight carbon atoms. In addition to halogen groups such as fluorine, chlorine, or bromine, the organic radical of the phosphite triester can be substituted with alkoxy or thioalkoxy groups, aryloxy or thioaryloxy groups, cyclohexyl or aryl groups, nitro groups or mixtures thereof.

The organic phosphite diester of the second step is substituted with the same moieties or mixtures thereof as the organophosphite triesters of the first step.

The use of an inert solvent is optional in both the first and second steps of the reaction. In the first step if no solvent is employed, the phosphite triester is metered slowly into a reservoir of the acylating agent at a rate slow enough to keep the temperature preferably below about 45° C., less preferably below about 60° C. Use of a solvent dissipates the heat by conduction and also by the heat of boiling. Selecting a solvent with a low boiling point is the preferred method for regulating the temperature, although any other means of temperature control may be used. Suitable solvents are methylene dichloride (b.p. 41° C.), ethylidene dichloride (b.p. 57° C.), chloroform (b.p. 61° C.), propyl chloride (b.p. 46° C.), tert-butyl chloride (b.p. 51° C.), and pentane (b.p. 36° C.).

In order to control the potential exotherm of the second step, it is normally carried out in a chilled vessel. The preferred temperature range for carrying out the addition of the phosphite diester is about 5°–20° C.; a less preferred upper limit is 35° C. For laboratory (gram) amounts a temperature of about 20°–35° C. is readily controllable. For pilot plant or commercial amounts (hundreds of kilograms) the temperature for the second step should be kept below about 15° C. The preferred solvent for the second step is methylene dichloride, but a solvent is not necessary.

Since the addition of the phosphite diester to the carbonyl bond of the phophonate and the rearrangement of the 1-hydroxyalkylidenediphosphonate are both base-catalyzed reactions, the presence of a weak base is preferred during these reactions (the second step). The ideal base is a low-boiling tertiary amine, so no chemical involvement can take place, and so that it is easily removed. Triethylamine (b.p. 89°) is strongly preferred. Less preferred are trimethylamine (b.p. 4°) for a highly chilled reaction, pyridene (b.p. 115° C.), or N-methylmorpholine (b.p. 115° C.). About three to about 20 percent by weight of the amount of phosphite diester is an appropriate amount of the tertiary amine to use in the second step. Within this range five to 15 weight percent of amine is preferred and about ten percent by weight percent of amine based on phosphite diester is highly preferred.

The length of reaction time for both the first and second steps can be varied over a wide range depending on the reagents and the temperatures employed. Normally, an appropriate time is about one hour for the controlled addition of the reagent for each step followed by about one hour of reaction time after addition for each step. In both steps the minimal addition time is established by control of the exotherm, which depends in large degree on the scale of the reaction (e.g. laboratory, pilot plane, commercial) and the means for controlling the temperature. There is no maximum length of time for carrying out each step, as long as the temperature is low enough to prevent degradation of the product.

After both steps of the process of the present invention have been performed the product is concentrated by evaporation of any low-boiling solvents and by-products at atmospheric pressure, or reduced pressure for solvents, excess reagents, or by-products boiling over about 80° C. at atmospheric pressure. Depending on the precise compound being prepared, most phosphoate-phosphonates will crystallize into a solid product after the second step has been completed and the temperature reduced to ambient or below, that is below about 25° C. The crystalline products are washed with water several times, then with dilute acidic solution to remove amine residues, water again, dilute base, and finally several water washings. The final post-preparative step normally is vacuum-drying.

The following examples illustrate certain embodiments of this invention but should not be interpreted as limiting the scope of protection which is sought.

EXAMPLE 1

This Examples illustrates the synthesis of a symmetrical phosphate-phosphonate.

A 1-liter three-necked, round-bottomed flask was equipped with a dropping funnel, reflux condenser, DRY ICE trap, thermometer, and magnetic stirrer. The flask was charged with 140.4 g (1 mole) of benzoyl chloride, and then 166 g (1 mole) of triethyl phosphite was added dropwise for an hour with stirring at a rate such that the temperature was maintained below 30° C. The solution became yellow within five minutes. After the addition of triethyl phosphite the stirred solution was heated for one and one-half hours at 40° C. During this time 15 ml of ethyl chloride was collected in the cold trap. Infrared analysis showed no benzoyl chloride remaining in the solution.

Then 200 ml of methylene chloride and 15 g of triethylamine were added and the solution chilled to 5° C. At this point dropwise addition of 138 g (1 mole) of diethyl phosphite was started at a rate of 3 ml/minute. After 30 minutes the solution was allowed to warm up to 26° C. at which temperature the addition was completed. After an hour of additional reflux the solvent was taken off by means of a rotary evaporator causing precipitation from the reaction mixture of 393 g of white crystals, which had an acid number of 5.9. The filtrate yielded 3.1 g of yellowish liquid having an acid number of 340.

The crystals were dissolved in methylene chloride, washed with water, and vacuum dried at 1.5 torr at 95° C. for three hours yielding 360 g of white crystals with a hydroxyl number of 3.6, an acid number of 0.6, and an elemental analysis of 16.0% P (calculated P for tetraethylbenzal phosphate-phosphonate 16.3%). The yield was 96 percent. The $^{31}$P and $^1$H nuclear magnetic spectra for the product were consistent with the postulated structure.

EXAMPLE 2

Example 2 illustrates the synthesis of a haloalkyl phosphate-phosphonate using a solvent for both steps of the preparation.

The same equipment and procedure as in Example 1 was employed. In the first step 100 g methylene chloride was the solvent to which 70 g (0.5 mole) benzoyl chloride was charged. Tris ($\beta$-chloroethyl phosphite in the amount of 135 g (0.5 mole) was added dropwise for 15 minutes at room temperature with no evidence of exotherm. The temperature was increased to 50° C. with no evidence of exotherm as the addition of the phosphite triester was completed over 60 minutes. At the conclusion of the addition of reagent the first step reaction mixture was held at reflux (60° C.) for four hours. The next day the reaction was continued for four additional hours at reflux (60° C.) until the amount of residual benzoyl chloride did not diminish, as shown by infrared analysis. The solvent was removed by means of a rotary evaporator at 10 torr and 50° C. yielding 160 g of liquid showing a homogeneous composition by $^{31}$P and $^{13}$C nuclear magnetic resonance spectroscopy.

For the second step a flask was charged with 100 g of methylene chloride, 90 g (0.43 mole) of bis ($\beta$-chloroethyl) phosphite diester, and 10 g of triethylamine. Then 140 g of the product of step one dissolved in 50 g of methylene chloride was added dropwise at 15° C. for 30 minutes. After two hours reaction at 25° C. white crystals formed. The solvent was taken off for one hour at 25 torr and 40° C., and the product initially purified by means of a wiped-film apparatus at 115° C. at 1 torr followed by 150° C. at 0.8 torr. The yield was 225 g of tetra ($\beta$-chloroethyl) phosphate-phosphonate with a Cl content of 21.8%, P content of 11.9%, an acid number of 1.3, and a zero hydroxyl number (calculated for tetra ($\beta$-chloroethyl) benzal phosphate-phosphonate 28.29% Cl and 12.35% P). A $^{13}$C nuclear magnetic resonance spectrum was consistent with the postulated structure. Thermogravimetric analysis at 10° C./min in air showed transition points at 240° and 290° C. for the product.

EXAMPLE 3

Example 3 illustrates the synthesis of the tetra ($\beta$-chloroethyl phosphate-phosphonate of Example 2 on a larger scale.

A 2-liter three-necked, round-bottom flask was equipped as in Example 1 with the addition of a source of nitrogen gas for providing an inert atmosphere. After 30 minutes of nitrogen flow, the flask was charged with 420 g methylene chloride at 22° C., then 351.5 g (2.5 mole) of benzoyl chloride was added in bulk. The addition of 755 g (2.5 mole) of tris ($\beta$-chloroethyl) phosphite caused an exotherm to reflux (60° C.) and yellowing of the solution. During the night the solution returned to ambient temperature. At this point gas chromatographic analysis showed qualitatively that some phosphinyl compound has formed but some raw materials remained unreacted.

The next day the reaction was heated at 60° C. reflux for two hours. After one-half hour 15.3 g benzoyl chloride was added. After a second half-hour an additional 10 g benzoyl chloride was added, whereupon the reaction mixture was kept at reflux for four hours and then stirred all night at ambient temperature.

On the third day the reaction flask was brought to 10° C. whereupon 50 g of triethylamine was added without exotherm. The reaction vessel was then chilled to 5° C., and dropwise addition of 520 g of bis ($\beta$-chloroethyl) phosphite with 20 g methylene chloride to lower viscosity was carried out over the period of an hour. During this hour the temperature of the mixture was kept below 25° C. When the ice was removed from the water bath, the exotherm carried the temperature to 32° C. White crystals started to form at this point. Vacuum distillation was then carried out at 50° C. and 40 torr with an aspirator. The reaction mixture was chilled to 0° C., the crystals filtered and dried by aspirator vacuum yielding 1256 g of the tetra ($\beta$-chloroethyl) phosphate-phosphonate.

The crude product was dissolved in methylene chloride, washed three times with water, once with 1% HCl, once with water, twice with 5% $K_2CO_3$ and then three times with water—all washings with 200 ml portions. After drying over magnesium sulfate, rotary vacuum evaporation was carried out at 50° C. and 1 torr to yield a final product weighing 1190 g with an acid number of 0.3. The calculated P content was 12.35%, observed 11.7%; calculated Cl content 28.29%, observed 25.1%. The $^{31}$P nmr spectrum was consistent with the postulated structure.

EXAMPLE 4

This Example illustrates the use of the product of Example 1 as a flame retardant (FR) in flexible polyurethane foam.

A flexible polyurethane foam with a cream time of 9 seconds, a rise time of 86 seconds, a density of 27.07 kg/m$^3$ and a porosity air flow of 1.51 l/sec (ASTM D-3574-77) was formulated containing 10 parts of the product of Example 1 for 100 parts of polyol (NIAX 16-46), 50 parts of toluene diisocyanate 80/20 and minor amounts of catalyst and surface active agent.

The DOT Federal Motor Vehicle Safety Standard Flammability Test 302 (horizontal burning) was carried out with the satisfactory result of 0.4 cm self-extinguishing non-burning rate. The General Motors cycle test for permanence (Fisher Body Material Sepcification 7-5) was also passed satisfactorily. The California Standard (Bulletin 117) vertical burn test for furniture foam was not passed. One sample burned two cm for three seconds after the 12-second application of flame at this level of loading (1% P).

EXAMPLE 5

This Example illustrates the use of the product of Example 2 and a related product as flame retardants in flexible polyurethane foam.

The same flexible foam formulation as in Example 4 was used to prepare two foam sample flame retardants: Foam A, the tetra ($\beta$-chloroethyl) benzal phosphate-phosphonate of Example 2 at a level of 6.42 parts per hundred resin (0.5%), and Foam B, a tetraethyl methylene phosphate-phosphonate at a level of 9.1 parts per hundred resin (1% P). For foam A the cream time was 10 sec, the rise time 86 sec, the air flow was 1.03 l/sec and the density was 24.67 kg/m$^3$. For foam B the cream time was 10 sec, the rise time 89 sec, the air flow 2.3 l/sec and the density 28.04 kg/m$^3$ (ASTM D-3574-77).

Foam A had excellent self-extinguishing characteristics in the DOT Federal Motor Vehicle Safety Standard Test 302, a horizontal flammability test for automotive cushioning, both initially and after dry heat aging for 22 hours at 140° C.; rating SE, less than 3 cm burn. Foam A also passed the California Vertical Standard Test Bulletin 117) for flame retardance in furniture foam.

Foam B also passed the MVSS Test 302 flammability test for automotive cushioning with a rating of SENBR (self-extingusihing, no burning rate) less than 5 cm burn. Foam B also passed the California Vertical Standard Test (Bulletin 117) for flame retardancy in furniture foam.

EXAMPLE 6

This Example illustrates the preparation of a mixed alkyl acetylphosphate-phosphonate.

The same equipment and procedure as in Example 1 was employed. The reaction flask was charged with 100 ml ethylene dichloride and 85 g acetyl chloride (1.1 mole). The addition of 270 g (1.0 mole) tris ($\beta$-chloroethyl) phosphite was commenced dropwise and continued for one hour during which there was a slow exotherm to 35° C. After addition of the triphosphite the reaction continued with a self-maintained exotherm at about 40° C. for three hours and then a slow return to ambient temperature while stirring overnight. The pink acetyl bis($\beta$-chloroethyl) phosphite was isolated by rotary evaporatory at 50° C. and 15 torr. The yield was 261 g; acid number 2; purity by infrared analysis was about 75%.

For the second step a similar reaction flask was charged with 138 g (1.0 mole) diethyl phosphite 20 g triethylamine, and 100 ml methylene chloride under nitrogen. Over a period of 30 minutes the pink acetyl phosphonate made in step one above was dropped in causing an exotherm to reflux (48° C.) and formation of a yellow color. After one hour's reflux at 48° C. the reaction was stirred overnight with a return to ambient temperature. The 1-hydroxyethylidene-bis-phosphonate was isolated by rotary evaporation at 50° C. and 15 torr. Wiped film purification at 120° C. and 1 torr caused rearrangement of the 1-hydroxyethylidene bis-phosphonate to a mixture of the two isomeric diethyl-di($\beta$-chloroethyl)ethylidene phosphate-phosphonates in 75% overall yield 295 g. The acid number for the product was 2.8, the hydroxyl number 25, and the observed Cl 19.5%, P 15.2% (calculated for $C_{10}H_{22}O_7P_2Cl_2$ is Cl 18.3%, P 16.0%).

EXAMPLE 7

This Example illustrates the use of the mixed alkyl phosphate-phosphonate of Example 6 as a flame retardant in a flexible polyurethane foam.

The same polyurethane formulation as in Example 4 was employed with 16 parts of the product of Example 6 added for each 300 parts of NIAX 16-46 polyol and each 152 parts of toluene diisocyanate. The cream time was 10 sec, the rise time 81 sec, the air flow 2.1 l/sec, and the density 24.8 kg/m$^3$.

An Initial Motor Vehicle Safety Standard Flammability Test 302 for automotive cushioning was carried out on three samples of the foam sample made above with these results:

| Sample | Secs Burn | Cm Burned | Rating | Burn Rate cm/min |
|---|---|---|---|---|
| 1 | 0 | 0 | SE | 0 |
| 2 | 6 | 0.25 | SE/NBR | 2.5 |
| 3 | 7 | 0.75 | SE/NBR | 6.4 |

SE—self-extinguishing
NBR—no burning rate

The MVSS 302 Flammability Test was repeated after the foam sample had been heat-aged at 140° C. for 22 hours with these results:

| Sample | Secs Burn | Cm Burned | Rating | Burn Rate cm/min |
|---|---|---|---|---|
| 4 | 9 | 0.75 | SE/NBR | 5.0 |
| 5 | 8 | 0.75 | SE/NBR | 5.6 |
| 6 | 15 | 2.0 | SE/NBR | 8.0 |

A California Vertical Standard Test 117 (burning after 12 seconds of flame applied) was carried out on the sample of foam prepared above with these results:

| Sample | Additional Secs. Burned | Total Cm. Burned | Rating |
|---|---|---|---|
| 1 | 10 | 21.3 | Fail |
| 2 | 25 | 26.9 | Fail |
| 3 | 0 | 10.0 | Fail |
| 4 | 7 | 18.8 | Fail |
| 5 | 9 | 21.3 | Fail |

Another sample of flexible foam was prepared employing 24 parts of the product of Example 6 for each 300 parts of NIAX 16-46 polyol and each 152 parts of toluene diisocyanate. The cream time was 10 sec, the rise time 89 sec, the air flow 1.37 l/sec, and the density 24.4 kg/m$^3$.

The MVSS 302 Flame test for automotive cushioning was carried out on the sample containing the higher amount of the flame retardant of Example 6 both with and without heat aging for 22 hours at 140° C. with the result that there was no burning on any of the six samples leading to a rating of self-extinguishing. Also in the California Vehicle Test 117 for the foam sample containing the higher amount of this flame retardant none of the five samples burned after the initial application of flame for 12 seconds. The total average burn distance was 8.3 cm, leading to a Pass rating.

EXAMPLE 8

This Example illustrates the use of the tetra chloroalkyl product of Example 3 as a flame retardant for a polyester resin.

A polyester formulation was made up consisting of 100 g Resin 304-60 (Koppers Co., Pittsburgh, Penna.), 50 g aluminum hydroxide, 10 g product of Example 3, 2 ml methyl ethyl ketone peroxide, and 0.4 ml cobalt naphthenate. Upon mixing, this resin reached an unstirrable viscosity (cure time) in 12.4 minutes.

The National Bureau of Standards Smoke Chamber Test was carried out on plates of this resin with the result that an optical density reading of 391 was reached in 6.2 minutes and 442 in 5.3 minutes for an average reading of 416. The weight loss for these samples was 25.4 and 24.5% respectively.

The Underwriters Laboratory Flame Test 94 was carried out on a rod of this resin on five samples each flamed for 10 seconds twice. The average glow time after flaming was only 1 second with an average burn length of 3.75 cm. On all five samples cotton failed to ignite. These results lead to a passing classification of 94V-O.

The Limiting Oxygen Index test was run for two minutes on two samples of the polyester ester protected by the flame retardant system described above with oxygen index values of 29.40% (SE) and 29.93 (burn). When corrected by subtraction of 1.33, the final index rating was 28.60%.

The foregoing examples illustrate the instant invention for which the scope of legal protection sought is set forth in the following claims.

I claim:
1. A process for the preparation of organic phosphate-phosphonates comprising the steps of:
    (a) reacting an organic acylating agent with an organic phosphite triester to form an intermediate followed by
    (b) reacting the intermediate with an organic phosphite diester in the presence of from about 3 to about 20 percent by weight based on the weight of phosphite diester of a tertiary amine.
2. The process of claim 1 wherein the first step is carried out in the presence of a solvent.
3. The process of claim 1 wherein the second step is carried out in the presence of a solvent.
4. The process of claim 1 wherein the acylating agent is an acid chloride.
5. The process of claim 1 wherein the organic phosphite triester is an alkyl or haloalkyl phosphite.
6. The process of claim 1 wherein the organic phosphite diester is an alkyl or haloalkyl phosphite.
7. The process of claim 1 wherein the organic phosphite triester is triethyl phosphite.
8. The process of claim 1 wherein the organic phosphite diester is diethyl phosphite.
9. The process of claim 1 wherein the organic phosphite triester is tris($\beta$-chloroethyl)phosphite.
10. The process of claim 1 wherein the organic phosphite diester is bis($\beta$-chloroethyl) phosphite and the amine is triethylamine.
11. The process of claim 1 wherein the triester of the first step and the diester of the second step are based on different alcohol moieties, whereby a mixed organic phosphate-phosphonate is prepared.
12. The process of claim 1 wherein the acyl group of the acylating agent, the triester of the first step, and the diester of the second step are each based on different moieties, whereby an organic phosphate-phosphonate having three different substituents is produced.
13. A process for the preparation of organic phosphate-phosphonates comprising the steps of:
    (a) reacting benzoyl chloride with an organic phosphite triester to form an intermediate followed by:
    (b) reacting the intermediate with an organic phosphite diester in the presence of from about 3 to about 20 percent by weight based on the weight of phosphite diester of a tertiary amine.

* * * * *

UNITED STATES PATENT AND TRADEMARK OFFICE
CERTIFICATE OF CORRECTION

PATENT NO. : 4,407,765

DATED : October 4, 1983

INVENTOR(S) : SYNTHESIS OF ORGANIC PHOSPHATE-PHOSPHONATES

It is certified that error appears in the above–identified patent and that said Letters Patent are hereby corrected as shown below:

Column 4, line 48, "plane" should be -- plant --.

Column 4, line 60, "phosphoate-" should be -- phosphate- --.

Column 7, line 49, "self-extingusihing" should be

-- self-extinguishing --.

Signed and Sealed this

Fourteenth Day of February 1984

[SEAL]

Attest:

Attesting Officer

GERALD J. MOSSINGHOFF

Commissioner of Patents and Trademarks